(12) United States Patent
Shehri et al.

(10) Patent No.: US 10,401,278 B2
(45) Date of Patent: Sep. 3, 2019

(54) MICROWAVE HORN ANTENNAS-BASED TRANSDUCER SYSTEM FOR CUI INSPECTION WITHOUT REMOVING THE INSULATION

(71) Applicant: Saudi Arabian Oil Company, Dhahran (SA)

(72) Inventors: Ali Shehri, Thuwal (SA); Ayman Amer, Thuwal (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 255 days.

(21) Appl. No.: 15/616,535

(22) Filed: Jun. 7, 2017

(65) Prior Publication Data
US 2018/0356333 A1    Dec. 13, 2018

(51) Int. Cl.
*G01N 17/04* (2006.01)
*G01N 21/3563* (2014.01)
(Continued)

(52) U.S. Cl.
CPC .............. *G01N 17/04* (2013.01); *G01N 17/00* (2013.01); *G01N 21/3563* (2013.01);
(Continued)

(58) Field of Classification Search
CPC ...................................................... G01N 17/04
(Continued)

(56) References Cited

U.S. PATENT DOCUMENTS

| 5,491,409 A | 2/1996 | Flora et al. |
| 6,194,902 B1 | 2/2001 | Kuo |
| (Continued) | | |

FOREIGN PATENT DOCUMENTS

| WO | 2014127856 A1 | 8/2014 |
| WO | WO2016/057165 | 4/2016 |

OTHER PUBLICATIONS

Beardsley, P. et. al., "VertiGo—A Wall-Climbing Robot including Ground-Wall Transition," Disney Research. Dec. 29, 2015. Retrieved from https://www.disneyresearch.com/publication/vertigo/.
(Continued)

*Primary Examiner* — Christopher E Mahoney
(74) *Attorney, Agent, or Firm* — Leason Ellis LLP (57) ABSTRACT

The present disclosure is directed to methods and systems for inspecting insulated equipment for any corrosion under insulation (CUI). The system includes a device comprising transmitter and receiver horn antennas, a vector network analyzer operatively connected to the antennas, and an infrared detector. In the method, a location for inspection of the equipment is identified. A metal jacket surrounding the location is removed without stripping the insulation. Microwaves are transmitted by the transmitted horn antenna at the location, and provide heating at the location. The microwaves are received by the receiver horn antenna after reflection off the equipment. The vector network analyzer analyzes the microwaves. The infrared detector detects infrared waves emitted from the location and develops an infrared image of the inner surface of the equipment. Based on the analysis of the microwaves and the developed image, a programmed processor determines whether CUI exists at the location.

22 Claims, 5 Drawing Sheets

(51) Int. Cl.
*G01N 22/02* (2006.01)
*G01R 27/28* (2006.01)
*G01N 25/72* (2006.01)
*G01N 17/00* (2006.01)
*G01N 22/04* (2006.01)

(52) U.S. Cl.
CPC ............. *G01N 22/02* (2013.01); *G01N 22/04* (2013.01); *G01N 25/72* (2013.01); *G01R 27/28* (2013.01)

(58) Field of Classification Search
USPC .................................................. 324/639, 644
See application file for complete search history.

(56) References Cited

U.S. PATENT DOCUMENTS

| | | |
|---|---|---|
| 6,570,379 B2 | 5/2003 | Crouzen et al. |
| 8,596,861 B2 | 12/2013 | Kane et al. |
| 9,091,664 B2 | 7/2015 | Krause et al. |
| 9,518,918 B2 | 12/2016 | Mann |
| 2012/0056634 A1 | 3/2012 | Bohon et al. |
| 2016/0003734 A1* | 1/2016 | Mann ................... G01N 17/006 250/339.05 |
| 2016/0146658 A1* | 5/2016 | Littleford .............. G01F 23/284 342/124 |

OTHER PUBLICATIONS

B-Unstoppable, World First TankCopter. Retrieved from https://www.indiegogo.com/projects/b-unstoppable-world-s-first-tankcopter-drone-gadget-technology#/ . (2015).
'B' the Flying car. Retrieved from https://www.kickstarter.com/projects/2017062404/b-go-beyond/description . May 2013.
Riggs, K. et al., "Drones Help Detect Corrosion under Insulation," Materials Performance. Retrieved from http://www.materialsperformance.com/articles/materialselectiondesign/2016/06/droneshelpdetectcorrosionunderinsulation. Jun. 7, 2016.
Jones, R., "Use of Microwaves for the Detection of Corrosion under Insulation," Department of Mechanical Engineering. Imperial College London. Apr. 2012.
International Search Report and Written Opinion in corresponding International Patent Application No. PCT/US2018/034561, dated Sep. 18, 2018. 16 pages.
No Author. "Introduction to VNA Basics." Tektronix. Mar. 1, 2017 (Mar. 1, 2017), XP055505828, 21-23. Retrieved from the Internet: URL:http://download.tek.com/document/70W_60918_0_Tek_VNA_PR1.pdf [retrieved-on Sep. 10, 2018]. 20 pages.

* cited by examiner

MICROWAVE HORN ANTENNAS-BASED TRANSDUCER SYSTEM FOR CUI INSPECTION WITHOUT REMOVING THE INSULATION

FIELD OF THE INVENTION

The present invention relates to a system and process for inspecting insulated equipment for corrosion under insulation, and more specifically relates to nondestructive testing systems and methods for evaluating insulated equipment for any corrosion under insulation.

BACKGROUND

Corrosion under insulation (CUI) is a particular type of corrosion that can occur in insulated equipment (e.g., piping) due to moisture build-up on the external surface of the insulated equipment. CUI that remains undetected can cause severe damage to the equipment (e.g., equipment failure), and thereby result in the closure of a process unit that features the damaged equipment or even a shutdown of an entire facility if the CUI occurs in a particularly vital location. The precursor of CUI is the accumulation of moisture and the development of water patches underneath insulation layers of the equipment.

For insulated pipes, the structure of the pipe generally includes several layers, including (starting from the inside and moving outward): a compatible coating, the insulation material, and a metal jacket cladding. The insulation material in the equipment generally comprises fibrous material (e.g., glass/mineral wool) and/or cellular material (e.g., calcium silicate, polyurethane, polystyrene). The cladding acts as a protective barrier on the outside of the piping, protecting the pipe from the outside elements (e.g., weather). For example, the cladding helps to prevent the insulation from being exposed to rain or physical damages.

Conventionally, in order to inspect insulated equipment for CUI, the portion of the equipment to be inspected is stripped of its cladding and its insulation, and is then visually inspected to see if CUI exists. This current practice, however, is time consuming because locations along the equipment must be checked at random or on a schedule, as there is oftentimes no outward indication of CUI. Further, the current practice is costly, as the insulation must be replaced at every inspection location, regardless of whether CUI was discovered or not. Accordingly, there is a need for a more time-effective and cost-effective process for inspecting insulated equipment for CUI. The present invention addresses one or more of these and other needs.

SUMMARY

According to an aspect of the present invention, systems and methods for inspecting insulated equipment (e.g., pipe) for corrosion under insulation are provided. The present systems and methods allow for inspection of the insulated equipment.

In a first aspect, a system includes a portable, dual detection device comprising a transmitter horn antenna and a receiver horn antenna. The transmitter horn antenna is configured to transmit microwaves toward the insulated equipment at a selected location on the insulated equipment, and the receiver horn antenna is configured to receive the transmitted microwaves after reflection from the insulated equipment at the selected location. According to an aspect of the present invention, the microwaves are radio waves. According to another aspect, the microwaves have a frequency in the range of approximately 30 MHz to approximately 300 GHz.

In one implementation, the system also includes or communicates with a vector network analyzer operatively connected to the transmitter and receiver horn antennas. The vector network analyzer is configured to analyze the power of the transmitted and received microwaves. The system further includes an infrared detector configured to detect infrared waves emitted from the insulated equipment and to develop an image of the inner surface of the insulated equipment at the selected location based on the detected infrared waves. The system also includes a controller having a memory storing instructions in the form of code, and a processor configured by executing the instructions. The controller is configured to enable operations of the transmitter and receiver horn antennas, the vector network analyzer, and the infrared detector.

According to one aspect, the transmitter and receiver horn antennas are operatively connected to the vector network analyzer via waveguide cables. According to another aspect, the vector network analyzer includes a directional coupler that is configured to focus the transmitted microwaves at the selected location on the equipment. According to a further aspect, the vector network analyzer is further configured to determine the length of a signal path of the microwaves from the transmitter horn antenna to the receiver horn antenna.

According to another aspect, the system can also includes a time-of-flight microwave camera configured to capture microwaves in flight from the transmitter horn antenna and develop time-resolved imaging and/or 3D imaging based on the captured microwaves.

According to another aspect, the system includes a scanning holder operatively connected to the transmitter and receiver horn antennas, and configured to maintain the transmitter and receiving horn antennas at respective fixed distances from the selected location.

According to another aspect, the system components are housed on an unmanned aerial vehicle (UAV). According to a further aspect, the UAV comprises a rangefinder configured to measure the depth of the UAV and maintain the UAV at a fixed position relative to the selected location.

According to another aspect, the transmitting and receiving horn antennas can be aligned to face one another to form a line-of-sight configuration, and the vector network analyzer can be configured to perform free space dielectric measurements on the insulated equipment at the selected location.

According to another aspect, a method for inspection of the insulated equipment for corrosion under insulation is provided. In the method, a location on the insulated equipment that is suspected of corrosion under insulation is identified. A metal jacket surrounding the insulated equipment at the identified location is removed without stripping the insulation from the equipment. Microwaves are transmitted by the transmitted horn antenna towards the insulated equipment at the identified location, such that the transmitted microwaves provide heating at the location. The transmitted microwaves are then received by the receiver horn antenna after reflection of the microwaves off the insulated equipment. The vector network analyzer then analyzes the transmitted and reflected microwaves. The infrared detector detects infrared waves emitted from the location of the insulated equipment, and then develops an image of an inner surface of the insulated equipment underneath the insulation at the identified location based on the detected infrared waves. Based on the analysis of the transmitted and reflected microwaves and the developed image, a determination is made by the processor as to whether any corrosion under insulation exists at the location.

According to another aspect, in the analysis of the transmitted and reflected microwaves, the power of the microwaves is measured at the time of transmission by the transmitting horn antenna and at the time of reception by the receiving horn antenna. Further, a power difference in the microwaves at the time of transmission versus at the time of reception is determined. According to another aspect, in the analysis of the transmitted and reflected microwaves, the length of the signal path of the microwave from the transmitter horn antenna to the receiver horn antenna is determined.

According to another aspect, the determined power difference and the length of the signal at the identified location are compared with a power difference and a length of signal for a calibrated reference insulated equipment to determine an amount of wall thickness loss at the identified location.

According to another aspect, the two horn antennas are maintained at a fixed distance from the identified location on the insulated equipment during transmission and reception of the microwaves. According to another aspect, transmission, reception, and analysis of the microwaves occurs at substantially the same time as the detection of infrared waves and the development of the infrared image.

According to another aspect, a metal jacket is reinstalled around the insulated equipment at the identified location. According to another aspect, the power of the received microwaves is a function of a distance between the transmitter horn antenna and the receiver horn antenna, a frequency of the transmitted microwaves, a power of the transmitter horn antenna, and a gain of the transmitter horn antenna. According to another aspect, the developed image of the surface of the insulated equipment at the identified location shows the geometry of the inner surface of the insulated equipment underneath the insulation.

BRIEF DESCRIPTION OF THE DRAWINGS

Further aspects of the present disclosure will be more readily appreciated upon review of the detailed description of its various embodiments, described below, when taken in conjunction with the accompanying drawings, of which.

DETAILED DESCRIPTION CERTAIN OF EMBODIMENTS OF THE INVENTION

By way of overview and introduction, the present disclosure details systems and methods for inspecting insulated equipment for corrosion under insulation (CUI) using a microwave horn antennas-based transducer system. Despite the understanding in the field that CUI can cause immense damage to insulated equipment, conventional processes for identifying and repairing areas of the equipment damaged by CUI are time-consuming and costly due to the inability to accurately identify damaged equipment areas without removing the insulation for visual inspection. As such, in an effort to improve the efficiency and cost-effectiveness of the inspection, the systems and methods as described herein provide a series of operations in which insulated equipment is assessed for possible CUI damage without having to remove the insulation in the equipment.

More specifically, in accordance with at least one embodiment of the present application, a microwave horn antennas-based transducer system is provided for inspection of insulated equipment at selected locations. The system generally includes a pair of horn antennas—specifically, a transmitter horn antenna and a receiver horn antenna. The transmitter horn antenna transmits microwaves toward the insulated equipment, while the receiver horn antenna receives the transmitted microwaves after reflection off of the insulated equipment. The system also includes, or communicates with, a vector network analyzer that is connected to the horn antennas and is configured to analyze the power of the transmitted and received microwaves. The system can also feature an infrared detector that detects infrared waves transmitted from the insulated equipment, which are used to develop an image of the inner surface of the insulated equipment.

Accordingly, the vector network analyzer analyzes the transmitted and reflected microwaves (signals), and the infrared detector simultaneously images the insulated equipment at the selected locations. The transmitted microwaves also provide heat to the selected locations, which facilitates infrared imaging that is highly sensitive and thus allows for the detection of hidden water accumulation in the insulated equipment. Thus, based on an analysis of the transmitted and received microwaves and the image of the inner surface of the equipment, the system can determine whether CUI (or precursors of CUI) exists at the selected locations on the equipment. In particular, the system can provide direct detection of wall thickness loss in the insulated equipment (which is symptomatic of CUI) via the microwave analyses and indirect detection of precursors of CUI, such as water spots and moisture, via infrared imaging.

In one or more embodiments, the system can further include a time-of-flight microwave camera configured to capture microwaves in flight from the transmitter horn antenna and develop time-resolved imaging and/or 3D imaging based on the captured microwaves. In at least one implementation of this embodiment, a single illumination source can be is used for releasing bursts of microwaves. The time-of-flight camera then tracks how long it takes for the microwaves to bounce off something (e.g., a portion of the pipe) and return to the camera. The signal transmitted by the illumination source can sweep with a constantly changing frequency. The frequency of the reflected signal is then compared with the frequency of the signal transmitted at that moment. The difference between these frequencies is proportional to the distance from the sensor to the surface of the equipment. The signal levels of the transmitted microwaves can be measured and analyzed in comparison to the resulted spectra from the water absorption areas and reflection variations from the pipe surface geometry.

The following detailed description is directed to the microwave horn antennas-based transducer systems and methods for using these systems for inspecting insulated equipment for CUI. While the following detailed description describes, in part, methods for inspecting equipment for CUI, it should be understood that these methods can also be used to inspect equipment for other types of corrosion or damage, such as leaks or other water damage. The referenced systems and methods are now described more fully in reference to the accompanying drawings, in which one or more illustrated embodiments and/or arrangements of the systems and methods are shown. The systems and methods are not limited in any way to illustrated embodiments and/or arrangements as the illustrated embodiments and/or arrangements described herein are merely exemplary of the present systems and methods, which can be embodied in various forms as appreciated by those skilled in the art. Thus, it should be understood that any structural and functional details disclosed are not to be interpreted as limiting the present systems and methods, but rather are provided herein as representative embodiments and/or arrangements for teaching a person of skill in the art one or more ways to implement the present systems and methods.

Accordingly, aspects of the present systems and methods can take the form of an entirely hardware embodiment, or an embodiment combining software and hardware. One of skill in the art can appreciate that a software process can be transformed into an equivalent hardware structure, and a hardware structure can itself be transformed into an equivalent software process. Thus, the selection of a hardware implementation versus a software implementation is one of design choice and left to the implementer. Furthermore, the terms and phrases used herein are not intended to be limiting, but rather, are to provide an understandable description of the systems and methods.

Figure 1A:
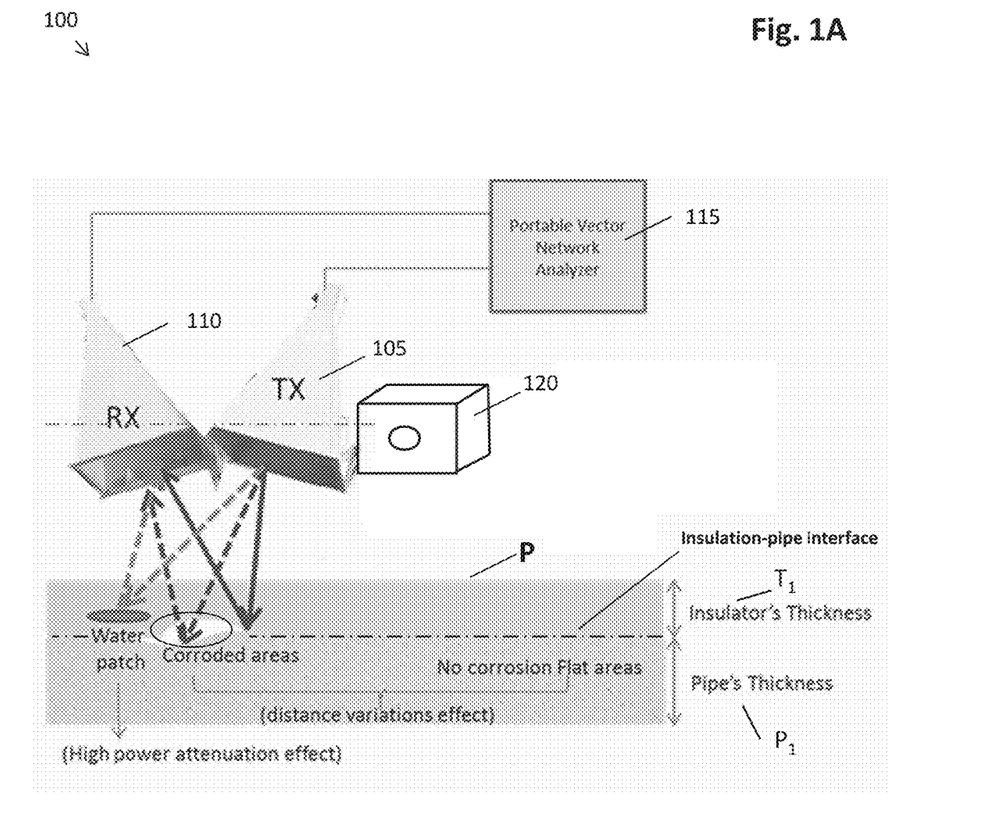
FIG. 1A is a diagram of an exemplary system for inspecting insulated equipment in accordance with one or more embodiments.

An exemplary system 100 for inspecting insulated equipment, in accordance with one or more embodiments, is shown at FIG. 1A. As shown in FIG. 1A, the system 100 can include a transmitter horn antenna 105 and a receiver horn antenna 110. The transmitter horn antenna 105 is configured to transmit microwaves toward a site or location on the insulated equipment (in this embodiment, a pipeline "P") to be inspected. Likewise, the receiver horn antenna 110 is configured to receive the microwaves transmitted from the transmitter antenna 105 after the microwaves have reflected off of the inspected area on the equipment. The transmitter and receiver horn antennas are maintained at a fixed distance from the pipe during the inspection process to ensure that detected variances in the microwave signals are accurate and, thus, indicative of surface variations in the insulated equipment. In an alternative embodiment, the system can comprise multiple transmitter and receiver horn antennas. In at least one implementation, the horn antennas provide high directivity of the microwaves towards the inspected equipment. In one or more implementations, the microwaves transmitted and received by the horn antennas are radio waves. In one or more implementations, the frequency range for the transmitted microwaves is approximately 30 MHz to approximately 300 GHz. In at least one implementation, the frequency range for the transmitted microwaves is approximately 2 GHz to approximately 300 GHz. In certain implementations, the frequency range for the transmitted microwaves is approximately 2 GHz to approximately 3 GHz. In at least one implementation, the frequency of the transmitted microwaves is approximately 2.4 GHz.

The horn antennas 105 and 110 are both operatively connected to a vector network analyzer 115. For instance, in certain implementations, the horn antennas 105, 110 are each connected to the vector network analyzer 115 via waveguide cables. The vector network analyzer 115 is configured to analyze the power of the transmitted and reflected microwave signals. In particular, the vector network analyzer 115 can be configured to measure the loss of power in the reflected microwaves received by the receiver antenna 110 relative to the power of the microwaves at transmission from the transmitter antenna 105. The difference in power between the reflected microwaves and the transmitted microwaves are used to help determine whether corrosion or moisture is present at the inspection area.

FIG. 1A shows an exemplary pipe configuration for the pipeline P, where the insulator has a thickness $T_1$ and the pipe underneath the insulator has a thickness $P_1$. The pipe and the insulator meet at an insulation-pipe interface denoted by the dashed line. As shown in FIG. 1A, the microwaves are transmitted from the transmitter horn antenna 105 toward the pipeline P. On the far left of pipeline P, the microwaves are shown being transmitted toward a water patch that is to be discovered and which is located below and within the insulation. In general, microwaves are greatly absorbed within a water medium and energy conservation occurs. When water absorbs microwaves, the microwaves are prevented from bouncing off the equipment and back to the receiver horn antenna. As such, a reduction in microwaves received by the receiver horn antenna is indicative of a water spot in the insulation. In other words, because a water medium can absorb microwave energy, a high attenuation effect is observed and thus a substantial decrease in power between the transmitted and reflected microwaves can signal that a water patch is present in the inspection area.

In analyzing the power of the transmitted and reflected microwaves, the vector network analyzer 115 can also consider other factors in its analysis including the frequency of the transmitted microwaves, variations in the pipe's metallic surface, radio frequency (RF) propagation loss equations (which are a function of the distance between the transmitter horn antenna 105 and the receiver horn antenna 110), and the gain of the transmitter horn antenna 105. For instance, with continued reference to FIG. 1A, microwaves are also shown being transmitted toward corroded areas of the pipe near the insulation-pipe interface. Corrosion on the pipe can cause deformations in the surface of the pipe relative to non-corroded areas of the pipe. Accordingly, a distance variance effect is measured between corroded and non-corroded areas of the pipe, as the distance transmitted microwaves must travel to the receiver antenna 110 is different when transmitted towards corroded areas versus non-corroded areas. For example, as shown in FIG. 1A, due to the deformations in the corroded areas of the pipe (circled area shown near the insulation-pipe interface), the microwaves transmitted at the corroded areas (dashed line) must travel a longer distance before they are reflected off of the pipe's surface towards the receiver antenna 110 relative to the microwaves transmitted at the non-corroded areas (solid line). As such, the distance traveled by the microwaves from the transmitter antenna 105 to the receiver antenna 110 varies depending on the amount of corrosion (e.g., deformation) on the pipe at the particular location, and the system by way of its programming computes these variations and differences.

In one or more embodiments, the vector network analyzer 115 can be configured to acquire the transmitted and reflected microwaves, and the resulting data can be transferred to and stored on a computing device (e.g., controller having a processor). The data regarding the reflections of the microwaves on the insulated equipment can be compared with a reference sample or a tested surface. The variations between the collected data from the equipment and the reference sample can reveal anomalies that are linked to wall loss and wall thinning of the equipment (e.g., pipe) due to corrosion. This type of corrosion is external and affects the external surface directly underneath the insulator. In the reference calibration sample, the physical dimensions and electrical characteristics (e.g., dielectric constant and effective dielectric constant) are known. For instance, characteristics of the insulator material plus the air dielectric constant (which equals 1) form the effective dielectric constant. Thus, in certain embodiments, the analysis of the inspected equipment can be compared with the measurements of a reference equipment (reference sample) that is not corroded or damaged to determine if corrosion is likely present in the inspected equipment by assessing any difference between the inspected equipment and the reference equipment.

As mentioned above, in one or more embodiments, the vector network analyzer 115 is configured to analyze the transmitted and reflected microwave signals to determine the amount of wall thickness loss (if any) at the selected inspection location, as wall thickness loss is an indication of CUI or other corrosion. The vector network analyzer 115 can determine whether wall thickness loss has occurred based on the length of the signal path of the microwave from the transmitter horn antenna 105 to the receiver horn antenna 110. In other words, the wall thickness loss (if any) is determined by analyzing the reflected signal amplitude attenuation as a function of the traveling distance of the transmitted microwaves. The signal path measurements at the selected inspection location can then be compared with measurements of a reference insulated equipment (a calibrated control specimen) to determine if wall thickness loss has occurred. In this comparison, if the signal path of the microwaves at the selected location is longer relative to the reference equipment, that indicates wall thickness loss at the selected location. In contrast, a shorter signal path for the microwaves at the selected location indicates a greater wall thickness relative to the reference equipment. For the reference insulated equipment (calibrated control specimen), it should be noted that its air dielectric constant (e.g., 1) plus the dielectric constant of the insulation must be considered in the calibration of the reference equipment.

As shown in FIG. 1A, in one or more embodiments, the transmitter horn antenna 105 and the receiver horn antenna 110 can be adjacent to one another during the inspection of a selected location along the insulated equipment. In an alternative embodiment, the transmitter and receiver horn antennas can face one another to form a line-of-sight configuration. In this embodiment, the vector network analyzer is configured to perform free space dielectric measurements on the insulated equipment at the selected location.

In one or more embodiments, the system 100 can further include an infrared wave detector 120 ("infrared detector" 120) that is configured to detect infrared waves emitted from the insulated equipment. The infrared detector 120 can also feature a camera configured to develop an infrared image of the insulated equipment at the inspection location based on the detected infrared waves. The camera can be part of the infrared detector 120 or, alternatively, a separate component that is operatively connected to the infrared detector 120. In one or more implementations, the infrared detector 120 has high sensitivity and accuracy in that it can differentiate between ambient temperature and the temperature of the insulated equipment, as discussed in further detail below.

Generally speaking, infrared waves (infrared radiation) are emitted by all objects (e.g., insulated equipment), with the amount of radiation emitted increasing as the temperature of the object increases. Accordingly, an infrared detector/camera can produce an image of an object based on the detected differences in temperature between the object and its background (i.e., the object and the background in the image are shown in different colors based on their temperature difference). In cases in which the object and its background have similar temperatures, an energy source can be used to increase the temperature of the object and, consequently, increase the radiation emitted by the object relative to its surroundings. The image produced by the infrared detector/camera 120 not only distinguishes between the object and its background based on the detected radiation of each, but also distinguishes the differences between different portions of the object based on the contrasting radiation.

In the present system 100, the infrared detector/camera 120 detects the radiation emitted from the equipment P and its background, and then develops an image, in conjunction with a processor configured by code implemented therein, based on the differences in emitted radiation between the equipment P and its background. Moisture formed in the backside of the insulation material gains (and loses) heat at different rates relative to the rest of the equipment, and thus emits radiation at different levels than other areas on the equipment P where moisture or CUI is not present. As such, the developed infrared image can also show differences not only between the equipment and its background, but also between different portions of the equipment P based on the contrasting radiation. Thus, the infrared detector/camera 120 provides the system 100 with a second way of detecting locations of possible CUI or moisture build up.

While radiation levels of the equipment are often distinguishable from its surrounding, differences in radiation levels at different portions of the equipment can be difficult to detect via an infrared detector/camera without an energy source (heat source). For instance, the basal temperature of a moisture-filled area may not differ significantly from the basal temperature of the remaining portions of the equipment. As such, directing an energy source at the equipment P can increases the temperature of the insulated equipment P at various spots throughout the selected inspection location, and thereby enhance the sensitivity of the infrared image for recognizing different radiation levels within the different portions of the equipment. In certain implementations, the sun can be used as an energy source for infrared imaging, which can enable effective detection of large patches of moisture or CUI. However, sun exposure can cause small moisture patches in the insulation material to evaporate quickly, thereby making it difficult to detect small areas of moisture accumulation in the insulation.

Accordingly, in at least one embodiment, the transmitted microwaves from the transmitter antenna 105 are not only used for the microwave analyses as discussed above, but are also used as an energy source (heat source) to enhance infrared imaging. The transmitted microwaves do not cause significant evaporation of insulation moisture to occur, and thus allows the infrared detector/camera to have greater sensitivity in detecting small areas of moisture accumulation in the equipment and for detecting soaked patches of insulation which can be difficult to distinguish during the day. As mentioned above, microwaves are greatly absorbed within a water medium and energy conservation occurs. When water is heated and absorbs microwaves, the microwaves are prevented from bouncing off the equipment and back to the receiver. As such, a reduction in microwaves received by the receiver horn antenna is indicative of a water spot. This heating process propagates to the surrounding areas of the insulated equipment as well (e.g., via a heat conduction mechanism), which make small, hidden wet areas larger and thus more detectable via an infrared detector/camera.

For example, during transmission of the microwaves by the horn antenna 105, the microwaves can be directed at a small area on the equipment, thereby providing heat to the small area. Once this small area is heated, heat will transfer into the surrounding insulation, which thereby allows for detection of large spots of moisture by the infrared imaging. In situations in which the equipment P is outside, the sun may be present during inspection, and can thus affect the radiation emitted by the equipment P and/or the evaporation levels in the equipment P. Thus, in one or more embodiments, inspections of the insulated equipment can be scheduled for times when evaporation due to sun exposure is unlikely to significantly affect the infrared detection and imaging, such as during the early morning or at night.

In one or more implementations, the system 100 can be handheld such that a user can easily move the system 100 between selected inspection locations along the insulated equipment. In at least one implementation, the system 100 can further include a support (e.g., scanning holder) that is configured to hold the horn antennas 105 and 110 at respective fixed distances from the inspection location on the pipe. The transmitter and receiver horn antennas are maintained at a fixed distance from the pipe during the inspection process to ensure that detected variances in the microwave signals are accurate and, thus indicative of surface variations in the insulated equipment.

Figure 1B:
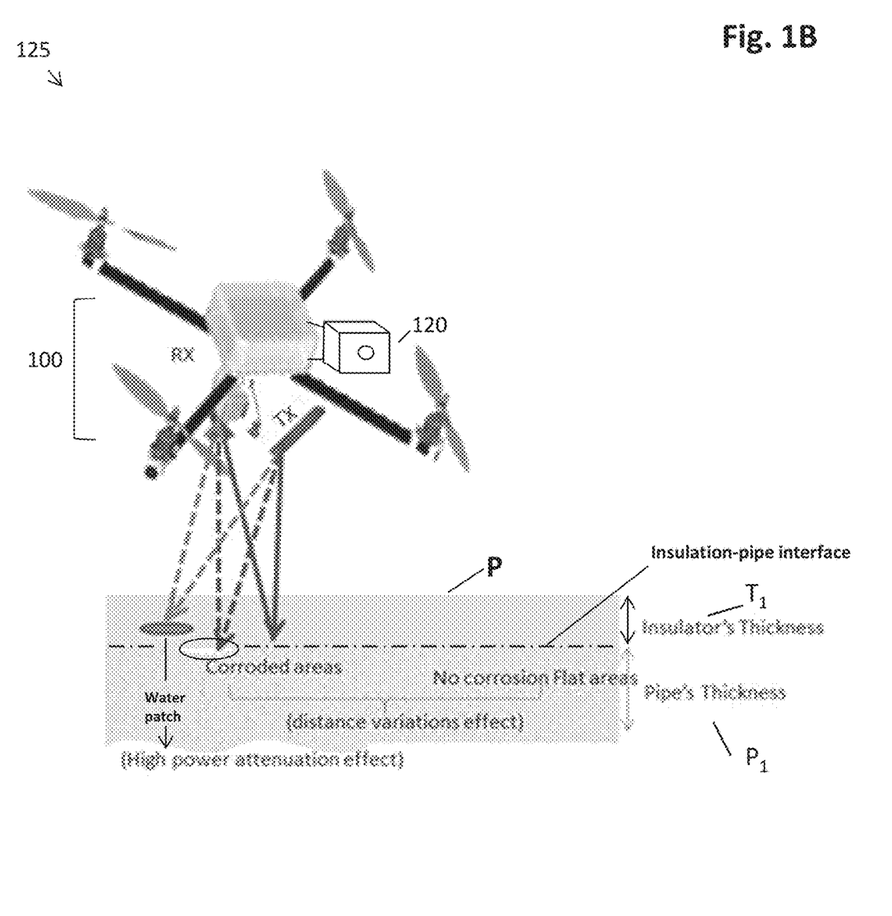
FIG. 1B is a diagram of another exemplary system for inspecting insulated equipment in accordance with one or more embodiments.

FIG. 1B shows another implementation of the present system, in which the system 100 is integrated as a module of a modular drone (or unmanned aerial vehicle) 125. The drone 125 allows a user to remotely inspect a location along a pipeline for CUI with the system 100. In certain embodiments, the drone 125 can also feature a rangefinder (altimeter) configured to measure the depth of the drone and maintain the drone at a fixed distance from the pipe during inspection to ensure accurate and consistent measurements. The rangefinder can be part of the same module as the system 100, or can be part of a separate module attached to the drone 125.

In one or more embodiments, the system 100 can further comprises a microwave beam focuser (directional coupler). The microwave bean focuser can be coupled to horn antennas 105 and 110, and is configured to focus the microwaves at specific critical locations on the insulated equipment. The vector network analyzer 115 can be configured to measure the reflection coefficient. The vector network analyzer 115 can also be configured to measure the incident and reflected power of the microwaves to determine voltage standing wave ratio (VSWR) and correlate the VSWR to the presence of water and/or wall thickness loss at the inspection location.

In at least one alternative embodiment, the system 100 can feature a camera sensitive to microwaves in place of a receiver horn antenna, where the camera acts as the receiver of the transmitted microwaves. In this embodiment, the camera provides time-resolved imaging that captures the microwaves in flight for time-of-flight computations by a programmed processor. The camera in this embodiment can also provide 3D imaging alone, or in conjunction with the programmed processor.

Further, in at least one implementation of this embodiment, a single illumination source, such as a frequency modulated continuous wave (FMCW) sensor is used for releasing bursts of microwaves. The time-of-flight camera then tracks how long it takes for the microwaves to bounce off something and return to the camera. The signal transmitted by the FMCW sensor sweeps with a constantly changing frequency. The frequency of the reflected signal is then compared with the frequency of the signal transmitted at that moment. The difference between these frequencies is proportional to the distance from the sensor to the surface of the equipment. The illumination bandwidth of the time-of-flight camera can identify the longer (deeper) defects as they reflect over the entire bandwidth, while the shorter defects (i.e., surface or superficial defects) reflect only the shorter wavelengths. In other words, the shorter defects are not as reflective of the longer wavelengths, thus causing them to appear more "blue" in color in the time-of-flight camera. The primary colors red, green, and blue represent the lower, middle, and upper frequency bands of illumination, respectively, in accordance with one or more implementations. The signal levels of the transmitted microwaves can be measured and analyzed in comparison to the resulted spectra from the water absorption areas and reflection variations from the pipe surface geometry.

In one or more embodiments, the system 100 can comprise a housing 130 that comprises the vector network analyzer 115, a power source 135 (e.g., battery), and a controller 140. The power source 135 can be configured to deliver power to the vector network analyzer 115 and to the horn antennas 105 and 110. In at least one implementation, the horn antennas 105 and 110 can have a separate power source.

Figure 2:
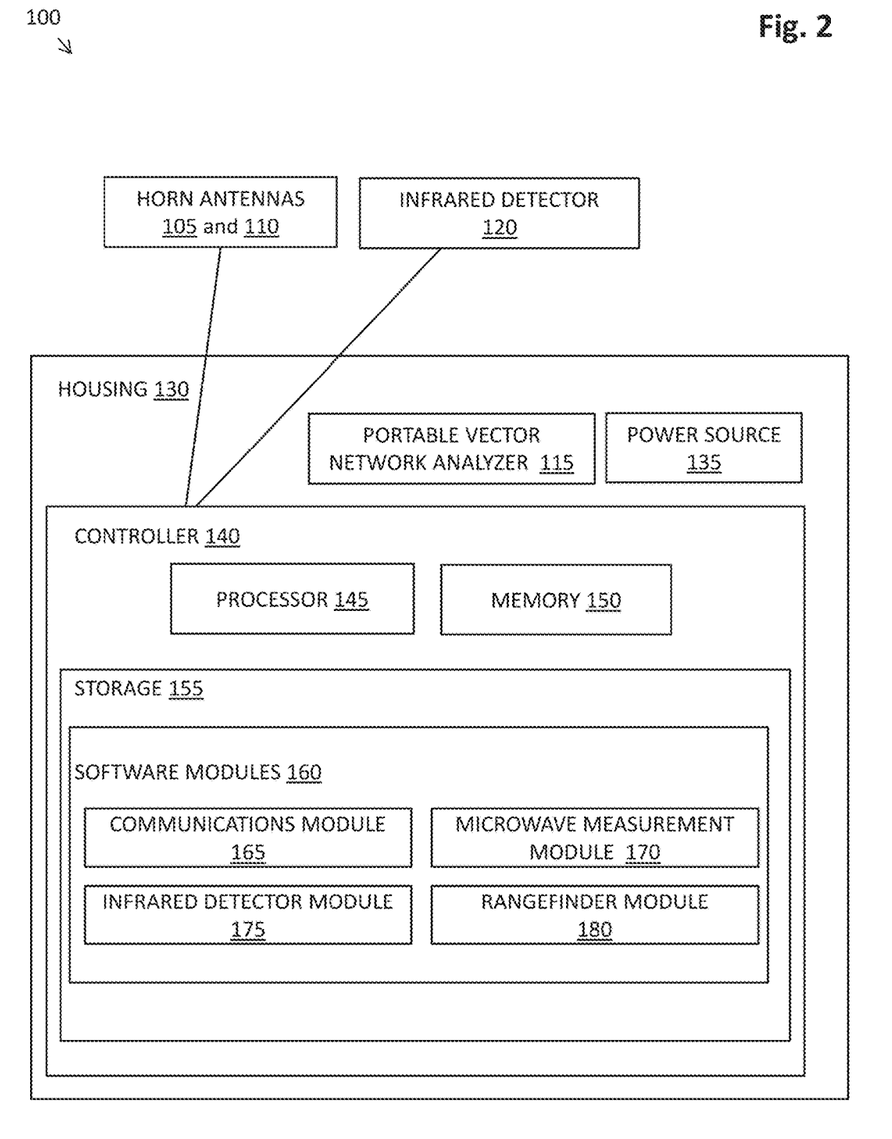
FIG. 2 is a block diagram illustrating an example configuration of the system for inspecting insulated equipment in accordance with one or more embodiments.

The controller 140 can be arranged with various hardware and software components that serve to enable various operations of the system 100, including a hardware processor 145, a memory 150, and storage 155. The processor 145 executes software instructions that can be loaded into the memory 150. The processor 145 can comprise a number of processors, a multi-processor core, or some other type of processor, depending on the particular implementation. In one or more embodiments, the controller 140 is operatively connected (e.g., wired or wireless connection) to the transmitter and receiver horn antennas 105 and 110, as well as the vector network analyzer 115 and the infrared detector 120, such that the controller 140 can enable various operations of the horn antennas 105/110, the vector network analyzer 115, and the infrared detector 120.

In one or more implementations, the memory 150 and/or the storage 155 are non-transient and accessible by the processor 145, thereby enabling the processor 145 to receive and execute instructions stored on the memory 150 and/or on the storage 155. The memory 150 can be, for example, a random access memory (RAM) or any other suitable volatile or non-volatile computer readable storage medium. In addition, the memory 150 can be fixed or removable. The storage 155 can take various forms, depending on the particular implementation. For example, the storage 155 can contain one or more components or devices such as a hard drive, a flash memory, a rewritable optical disk, a rewritable magnetic tape, or some combination of the above. The storage 155 also can be fixed or removable.

One or more software modules 160 are encoded in the storage 155 (as shown in FIG. 2) and/or in the memory 150. The software modules can comprise one or more software programs or applications having computer program code or a set of instructions implemented by or executed in the processor 145. Such computer program code or instructions for carrying out operations and implementing aspects of the systems and methods disclosed herein can be written in any combination of one or more programming languages. The program code can execute entirely on the system 100, as a stand-alone software package, partly on the system 100 and partly on a remote computer/device or entirely on such remote computers/devices. In the latter scenario, the remote computer systems can be connected to system 100 through any type of network, including a local area network (LAN) or a wide area network (WAN), or the connection can be made through an external computer (for example, through the Internet using an Internet Service Provider).

In one or more embodiments, included among the software modules 160 can be a communications module 165, microwave measurement module 170, an infrared detector module 175, and a rangefinder module 180 that are executed by processor 140. During execution of the software modules 160, the processor 145 is configured to perform various operations relating to the configuration of the system 100. In addition, it should be noted that other information and/or data relevant to the operation of the present systems and methods can also be stored on the storage 155, for instance various control programs used in the configuration of the system 100.

Similarly, in an alternative embodiment, the system 100 can include a control module (in place of the controller 140) that can be arranged with various hardware and software components that serve to enable operation of the system, including a processor, a memory, a communications module, a microwave measurement module, an infrared detector module, a rangefinder module 180, and a computer readable storage medium in order to execute the various functions of the system 100.

Figure 3:
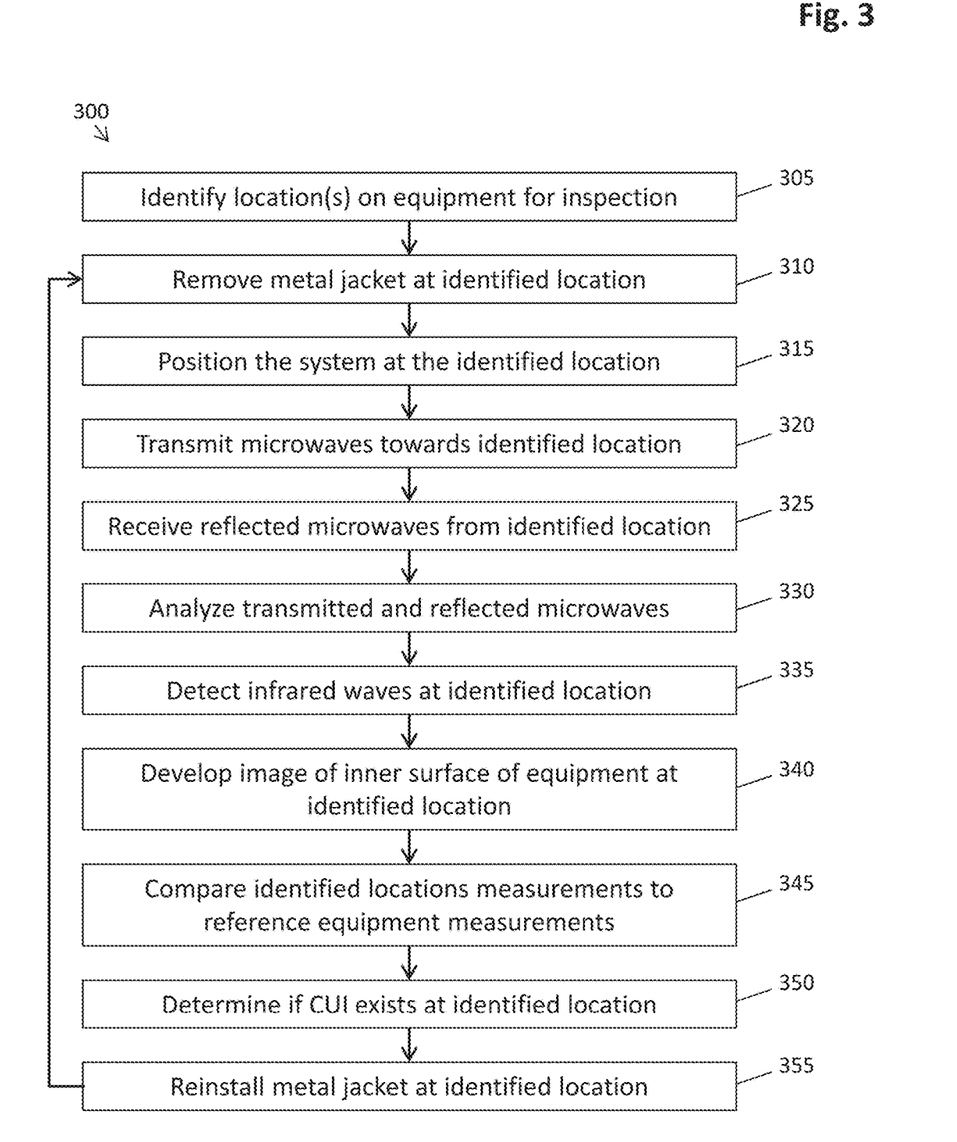
FIG. 3 is a flow diagram showing a routine that illustrates a broad aspect of the method for inspecting insulated equipment for corrosion under insulation in accordance with one or more embodiments.

With reference now to FIG. 3, a flow diagram is described showing a routine 300 (steps 305-355) that illustrates a broad aspect of the method for inspecting insulated equipment for CUI in accordance with one or more embodiments. It should be appreciated that several of the logical operations described herein are implemented (1) as a sequence of computer implemented acts or program modules running on system 100, and/or (2) as interconnected machine logic circuits or circuit modules within the system 100. The implementation is a matter of choice dependent on the requirements of the device (e.g., size, energy, consumption, performance, etc.). Accordingly, the logical operations described herein are referred to variously as operations, steps, structural devices, acts, or modules. As referenced above, several of these operations, steps, structural devices, acts and modules can be implemented in software, in firmware, in special purpose digital logic, and any combination thereof. It should be appreciated that more or fewer operations can be performed than shown in the figures and described herein. These operations can also be performed in a different order than those described herein. Further, some operations can be performed at substantially the same time as other operations.

The process begins at step 305, at which one or more locations for inspection on the insulated equipment are identified. Locations on the equipment can be identified in various ways, such as via a risk assessment process for identifying the most vulnerable areas on the insulated equipment. For instance, critical areas on the equipment, such as "dead legs" where water has accumulated and/or their nearby joints, can be identified as locations for inspection. In certain implementations, corrosion engineers can provide help as to where to inspect for corrosion.

At step 310, the metal jacket or cladding of the insulated equipment is removed at a selected location for inspection. In particular, while the cladding at the selected location is removed, the insulation that underlies the removed cladding is not removed and thus remains intact at the selected location. In one or more implementations, an operator or inspector can mechanically remove the metallic cladding prior to inspection.

At step 315, the system 100 is positioned at the selected location on the insulated equipment. In particular, the transmitter and receiver horn antennas are positioned at a fixed distance from the selected location in preparation for the inspection. In implementations in which the system 100 is handheld, the horn antennas can be maintained at the fixed distance from the selected location using a scanning holder. In implementations in which the system is integrated as a module on an unmanned aerial vehicle (drone), the processor 145 executing one or more software modules 160, including preferably rangefinder module 180, configures the drone to remain at a predetermined distance from the selected location on the insulated equipment.

At step 320, the processor 145 executing one or more software modules 160, including preferably microwave measurement module 170, configures the transmitter horn antenna 105 to transmit microwaves toward the selected location for inspection. In one or more implementations, the microwaves are transmitted for approximately 1 sec per 10 cm. As mentioned above, in one or more implementations, the transmitted microwaves are radio waves. Further, in at least one embodiment, the transmitted microwaves have a frequency in the range of approximately 30 MHz to 300 GHz.

At step 325, the processor 145 executing one or more software modules 160, including preferably microwave measurement module 170, configures the receiver horn antenna 110 to receive the microwaves after they have reflected off of the insulated equipment at the selected location.

At step 330, the processor 145 executing one or more software modules 160, including preferably microwave measurement module 170, configures the vector network analyzer 115 to analyze the transmitted and received microwaves.

Figure 4:
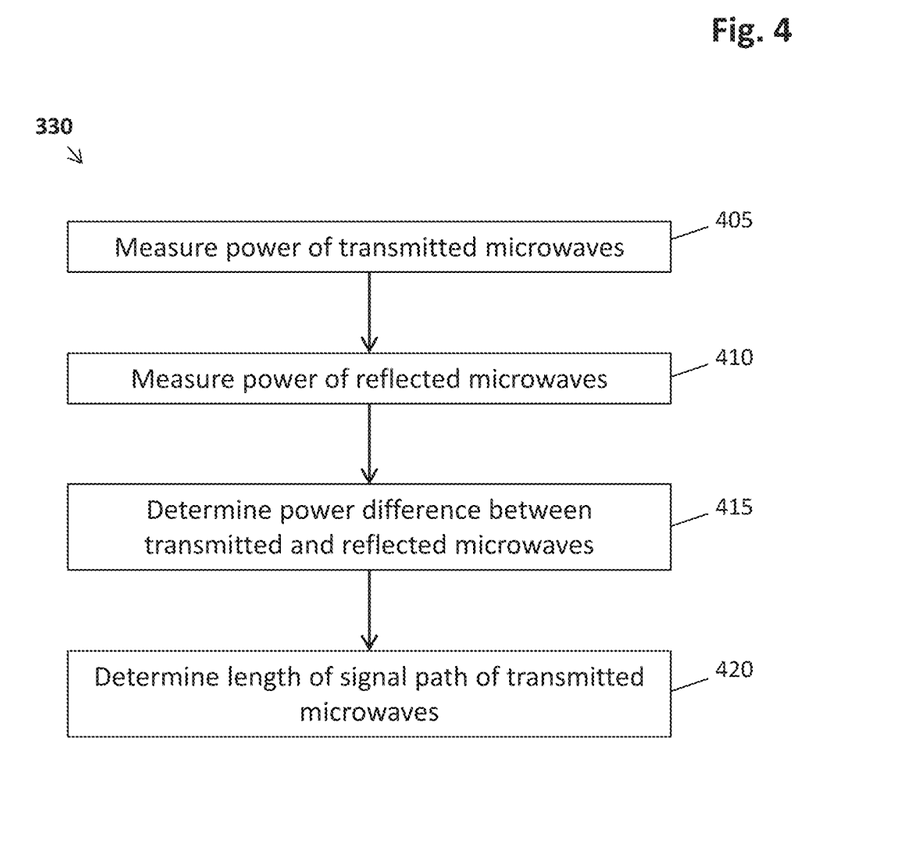
FIG. 4 is a flow diagram showing routine that illustrates an aspect of the method for inspecting insulated equipment for corrosion under insulation in accordance with one or more embodiments.

In one or more embodiments, step 330 can comprise one or more operations as shown in the routine of FIG. 4. With reference to FIG. 4, step 330 can comprises one or more of the steps 405-420. In particular, at step 405, the processor 145 executing one or more software modules 160, including preferably microwave measurement module 170, configures the vector network analyzer 115 to measure the power of the microwaves at transmission by the transmitter antenna 105. At step 410, the processor 145 executing one or more software modules 160, including preferably microwave measurement module 170, configures the vector network analyzer 115 to measure the power of the microwaves at reception by the receiver antenna 110. Then, at step 415 the processor 145 executing one or more software modules 160, including preferably microwave measurement module 170, configures the vector network analyzer 115 to determine a power difference between the transmitted microwaves and the received (reflected) microwaves.

As discussed above, the difference in power between the reflected microwaves and the transmitted microwaves are used to help determine whether corrosion or moisture is present at the inspection area. In particular, because a water medium can absorb microwave energy, a significant decrease in power between the transmitted and reflected microwaves can be resolved as being a signal that water is present in the inspection area. That signal can be displayed to a user or cause further action by the system to remediate and prevent or correct CUI.

At step 420, the processor 145 executing one or more software modules 160, including preferably microwave measurement module 170, configures the vector network analyzer 115 to determine the length of the signal path of the transmitted microwaves from the transmitter horn antenna 105 to the receiver horn antenna 110. The length of the signal path of the transmitted microwaves is used to determine the amount of wall thickness loss (if any) sustained at the selected inspection location, wherein wall thickness loss is an indication of CUI or other corrosion. The vector network analyzer 115 is configured to determine the length of the signal path by analyzing the reflected signal amplitude attenuation as a function of the traveling distance of the transmitted microwaves. These measurements at the selected inspection location can then be compared with measurements of a reference insulated equipment (as further discussed below) to determine if wall thickness loss has occurred.

Referring back to FIG. 3, in analyzing the power of the transmitted and reflected microwaves at step 330, the vector network analyzer 115 can also be configured to analyze other aspects of the microwaves, such as the frequency of the transmitted microwaves. The vector network analyzer 115 can be further configured, at step 330, to analyze features of the system 100 and/or the insulated equipment that can impact measurements of the microwaves, including variations in the pipe's surface at the selected location, the distance between the transmitter antenna 105 and the receiver antenna 110, radio frequency propagation loss, and antenna gain.

At step 335, the processor 145 executing one or more software modules 160, including preferably infrared detector module 175, configures the infrared detector/camera 120 to detect infrared waves emitted from the selected location of the insulated equipment. At step 340, the processor 145 executing one or more software modules 160, including preferably infrared detector module 175, develops an infrared image of the inner surfaces of the insulated equipment at the selected location based on the detected infrared waves from the infrared detector/camera 120. The infrared image of the selected location on the insulated equipment can allow for the detection of potential CUI and/or water accumulation based on the varying temperatures of certain portions of the insulated equipment (shown in different colors in the infrared image) relative to other portions of the equipment. In certain implementations, steps 335-340 can occur at substantially the same time as steps 320-330.

At step 345 the microwaves measurements and/or the infrared image at the selected location of the insulated equipment are compared with the microwaves measurements and/or an infrared image of a calibrated reference insulated equipment that is not corroded or damaged by water. Specifically, in one or more embodiments, the processor 145 executing one or more software modules 160, including preferably microwave measurement module 170 is configured to compare the difference in power between the reflected microwaves and the transmitted microwaves for the selected inspection location with the same difference in power for the reference equipment. Further, in one or more embodiments, the processor 145, executing one or more software modules 160 including preferably microwave measurement module 170, is configured to compare the length of the signal path of the transmitted microwaves at the selected inspection location with the length of the signal path of a calibrated reference equipment. In this comparison, if the signal path of the microwaves at the selected location is longer relative to the reference equipment, that indicates wall thickness loss at the selected location. In contrast, a shorter signal path for the microwaves at the selected location indicates a greater wall thickness relative to the reference equipment.

Still at step 345, in one or more embodiments, the processor 145, executing one or more software modules 160 including preferably infrared detector modules 175, is configured to compare the infrared image of the selected inspection location with an infrared image of a reference equipment. In certain implementations, step 345 is not computer-implemented, and thus the comparisons to the calibrated reference equipment can be completed by a user.

At step 350, a determination of whether CUI exists at the selected location is made. This determination can be based on the analysis of the microwaves (step 330), the developed infrared image of the selected location (340), and/or the comparison between the measurements at the selected location and the measurements of the reference equipment (step 345).

At step 355, a metal jacket is reinstalled at the selected location on the insulated equipment. In one or more implementations, an operator or inspector can mechanically reinstall the metallic cladding after the inspection. In certain embodiments, the metal jacket (cladding) that is reinstalled is a different (e.g., new) metal jacket as opposed to the metal jacket that was removed at step 305. In at least one embodiment, the metal jacket that is reinstalled is the same metal jacket removed at step 305, so long as the metal jacket was not damaged during its removal. After the metal jacket is reinstalled, the routine can return to step 310 if another location on the insulation equipment was identified for inspection at step 305.

It should be understood that although much of the foregoing description has been directed to systems and methods for inspecting insulated equipment for CUI, the system and methods disclosed herein can be similarly deployed and/or implemented in scenarios, situations, and settings far beyond the referenced scenarios (e.g., inspection of the insulated equipment for other types of damage). It should be further understood that any such implementation and/or deployment is within the scope of the system and methods described herein.

It is to be understood that like numerals in the drawings represent like elements through the several figures, and that not all components and/or steps described and illustrated with reference to the figures are required for all embodiments or arrangements. It should also be understood that the embodiments, implementations, and/or arrangements of the systems and methods disclosed herein can be incorporated as a software algorithm, application, program, module, or code residing in hardware, firmware and/or on a computer useable medium (including software modules and browser plug-ins) that can be executed in a processor of a computer system or a computing device to configure the processor and/or other elements to perform the functions and/or operations described herein. It should be appreciated that according to at least one embodiment, one or more computer programs, modules, and/or applications that when executed perform methods of the present disclosure need not reside on a single computer or processor, but can be distributed in a modular fashion amongst a number of different computers or processors to implement various aspects of the systems and methods disclosed herein.

Thus, illustrative embodiments and arrangements of the present systems and methods in part, provide a computer implemented method, a computer-based system, and/or a computer program product for inspecting insulated equipment for CUI. The flowchart and block diagrams in the figures illustrate the architecture, functionality, and operation of possible implementations of systems, methods and computer program products according to various embodiments and arrangements. In this regard, each block in the flowchart or block diagrams can represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprising" and/or "comprises", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present disclosure, which is set forth in the following claims.

What is claimed is:

1. A method for inspecting insulated equipment for corrosion under insulation using a portable, dual detection device comprising an infrared detector, a transmitter horn antenna, and a receiver horn antenna, the two horn antennas being operatively connected to a vector network analyzer, a controller having a memory storing instructions in the form of code, and a processor configured by executing the instructions therein, the method comprising:

identifying a location on the insulated equipment that is suspected of corrosion under insulation;
removing a metal jacket surrounding the insulated equipment at the identified location without stripping the insulation from the equipment;
transmitting, with the transmitter horn antenna, microwaves towards the insulated equipment at the identified location, wherein the transmitted microwaves provide heating at the identified location;
receiving, with the receiver horn antenna, the transmitted microwaves after reflection of the microwaves off the insulated equipment;
analyzing, with the vector network analyzer, the transmitted and reflected microwaves, wherein the step of analyzing comprises determining the length of a signal path of the microwave from the transmitter horn antenna to the receiver horn antenna;
detecting, with the infrared detector, infrared waves emitted from the identified location of the insulated equipment;
developing, with the infrared detector, an image of an inner surface of the insulated equipment underneath the insulation at the identified location based on the detected infrared waves; and
determining, with the processor, based on the analysis of the transmitted and reflected microwaves and the developed image, whether any corrosion under insulation exists at the identified location.

2. The method of claim 1, wherein the step of analyzing further comprises:
measuring the power of the microwaves at the time of transmission by the transmitting horn antenna and at the time of reception by the receiving horn antenna; and
determining a power difference in the microwaves at the time of transmission versus at the time of reception.

3. The method of claim 1, further comprising the step of:
comparing the determined power difference and the length of the signal at the identified location with a power difference and a length of signal for a calibrated reference insulated equipment to determine an amount of wall thickness loss at the identified location.

4. The method of claim 1, wherein the two horn antennas are maintained at a fixed distance from the identified location on the insulated equipment during the steps of transmitting and receiving.

5. The method of claim 1, wherein the insulated equipment is a pipe.

6. The method of claim 1, wherein the transmitting, receiving, and analyzing steps occur substantially simultaneously with the detecting and developing steps.

7. The method of claim 1, further comprising the step of:
reinstalling a metal jacket around the insulated equipment at the identified location.

8. The method of claim 1, wherein the microwaves are radio waves.

9. The method of claim 1, wherein the microwaves have a frequency in the range of approximately 30 MHz to approximately 300 GHz.

10. The method of claim 1, wherein the power of the received microwaves is a function of a distance between the transmitter horn antenna and the receiver horn antenna, a frequency of the transmitted microwaves, a power of the transmitter horn antenna, and a gain of the transmitter horn antenna.

11. The method of claim 1, wherein the developed image of the surface of insulated equipment at the identified location shows the geometry of the inner surface of the insulated equipment underneath the insulation.

12. A portable, dual system for inspecting insulated equipment for corrosion under insulation, the system comprising:
a transmitter horn antenna configured to transmit microwaves toward the insulated equipment at a selected location on the insulated equipment;
a receiver horn antenna configured to receive the transmitted microwaves after reflection from the insulated equipment at the selected location;
a vector network analyzer operatively connected to the transmitter and receiver horn antennas, wherein the vector network analyzer is configured to analyze the power of the transmitted and received microwaves and to determine the length of a signal path of the microwaves from the transmitter horn antenna to the receiver horn antenna;

an infrared detector configured to detect infrared waves emitted from the insulated equipment and to develop an image of the inner surface of the insulated equipment at the selected location based on the detected infrared waves; and a controller having a memory storing instructions in the form of code, and a processor configured by executing the instructions therein, wherein the controller is configured to enable operations of the transmitter and receiver horn antennas, the vector network analyzer, and the infrared detector.

13. The system of claim 12, wherein the transmitter and receiver horn antennas are operatively connected to the vector network analyzer via waveguide cables.

14. The system of claim 12, wherein the vector network analyzer comprises a directional coupler, wherein the directional coupler is configured to focus the transmitted microwaves at the selected location.

15. The system of claim 12, further comprising:
a time-of-flight microwave camera configured to capture microwaves in flight from the transmitter horn antenna and develop time-resolved imaging and/or 3D imaging based on the captured microwaves.

16. The system of claim 12, further comprising:
a scanning holder operatively connected to the transmitter and receiver horn antennas, and configured to maintain the transmitter and receiving horn antennas at respective fixed distances from the selected location.

17. The system of claim 12, wherein the system components are housed on an unmanned aerial vehicle (UAV).

18. The system of claim 17, wherein the UAV comprises a rangefinder configured to measure the depth of the UAV and maintain the UAV at a fixed position relative to the selected location.

19. The system of claim 12, wherein the insulated equipment is a pipe.

20. The system of claim 12, wherein the microwaves are radio waves.

21. The system of claim 12, wherein the microwaves have a frequency in the range of approximately 30 MHz to approximately 300 GHz.

22. The system of claim 12, wherein the transmitting and receiving horn antennas are aligned to face one another to form a line-of-sight configuration, and wherein the vector network analyzer is configured to perform free space dielectric measurements on the insulated equipment at the selected location.

* * * * *